United States Patent [19]

Sobin et al.

[11] Patent Number: 4,509,877

[45] Date of Patent: Apr. 9, 1985

[54] TAPERED TORQUE STRAIN RELIEF COUPLING

[76] Inventors: Sidney S. Sobin, 336 13th St., Del Mar, Calif. 92014; Daniel J. Netto, 153 N. Vendome St., Los Angeles, Calif. 90026

[21] Appl. No.: 550,050

[22] Filed: Nov. 9, 1983

[51] Int. Cl.³ .............................................. F16C 1/00
[52] U.S. Cl. ................................... 403/41; 285/114; 24/115 N
[58] Field of Search ................. 285/114; 403/41, 291; 339/104; 24/115 N

[56] References Cited

U.S. PATENT DOCUMENTS

| 289,381 | 12/1883 | Bodifield | 285/114 X |
|---|---|---|---|
| 656,187 | 8/1900 | Gunnell | 24/115 N |
| 2,143,985 | 1/1939 | Kellems | 24/123 |
| 2,189,987 | 2/1940 | Kellems | 339/63 R |
| 2,750,210 | 6/1956 | Trogdon et al. | 24/115 N |
| 2,813,730 | 11/1957 | Courtot | 24/115 N |
| 2,939,905 | 6/1960 | Canfield | 174/71 |
| 3,291,507 | 12/1966 | Clay | 285/114 |
| 3,487,160 | 12/1969 | Johnsen | 174/88 |
| 3,569,912 | 3/1971 | Damm | 339/101 |
| 4,070,083 | 1/1978 | DiPalma | 339/104 |
| 4,367,967 | 1/1983 | Albert, Jr. | 403/41 |

Primary Examiner—Andrew V. Kundrat
Attorney, Agent, or Firm—Fulwider, Patton, Rieber, Lee & Utecht

[57] ABSTRACT

A strain relief for the point of attachment of a flexible member to a rigid member, comprising a plurality of woven braided strands. The weaving is close or narrow at the point of attachment and progressively more open or wide along the flexible member as the distance from the point of attachment increases, distributing stress along the length of the flexible member.

15 Claims, 5 Drawing Figures

U.S. Patent  Apr. 9, 1985  Sheet 1 of 3  4,509,877
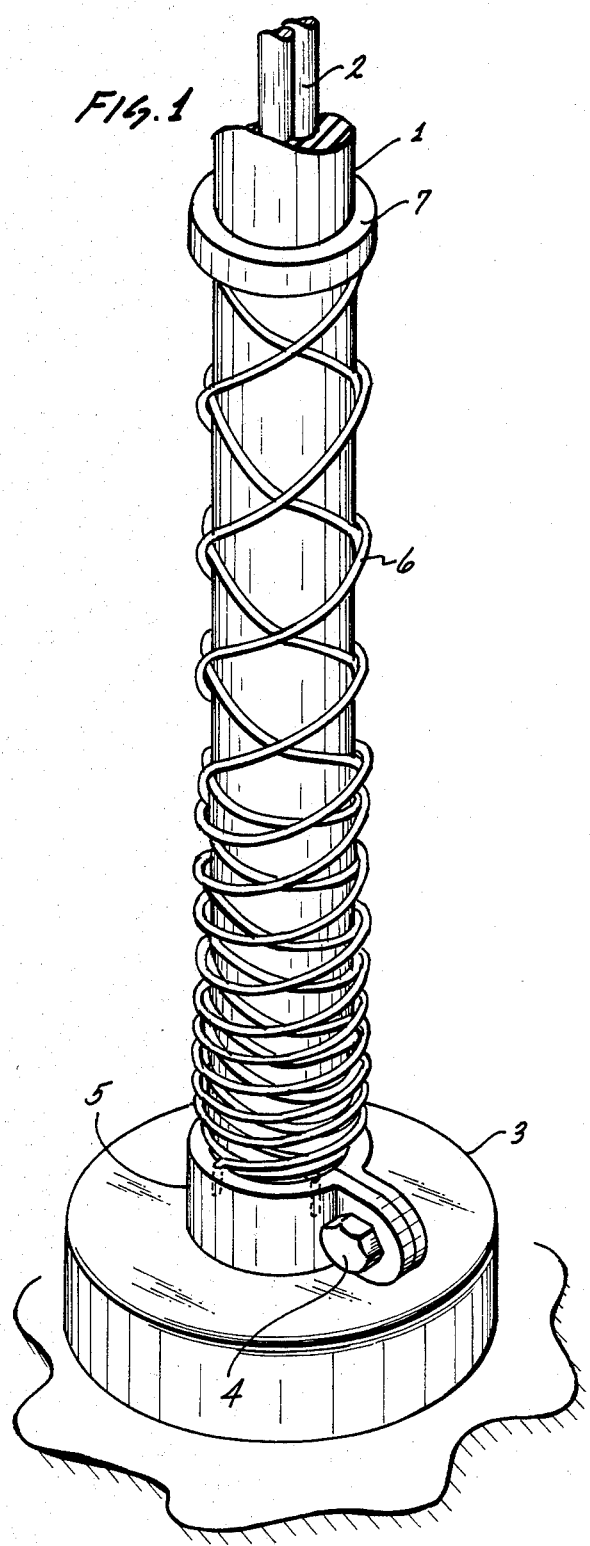
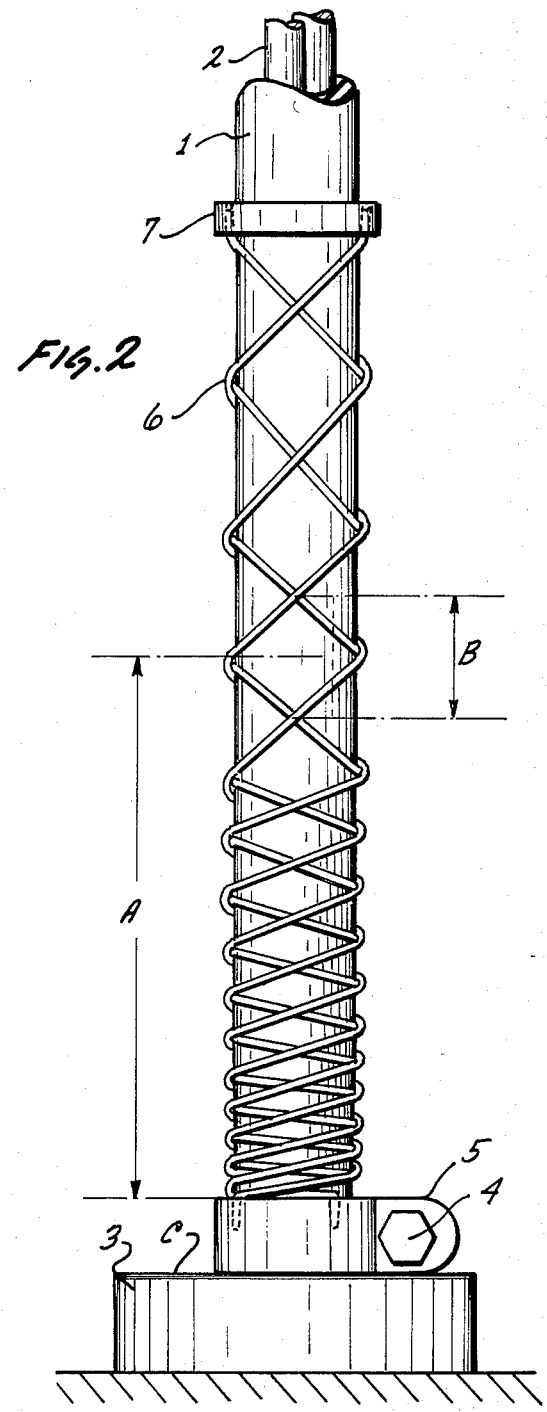

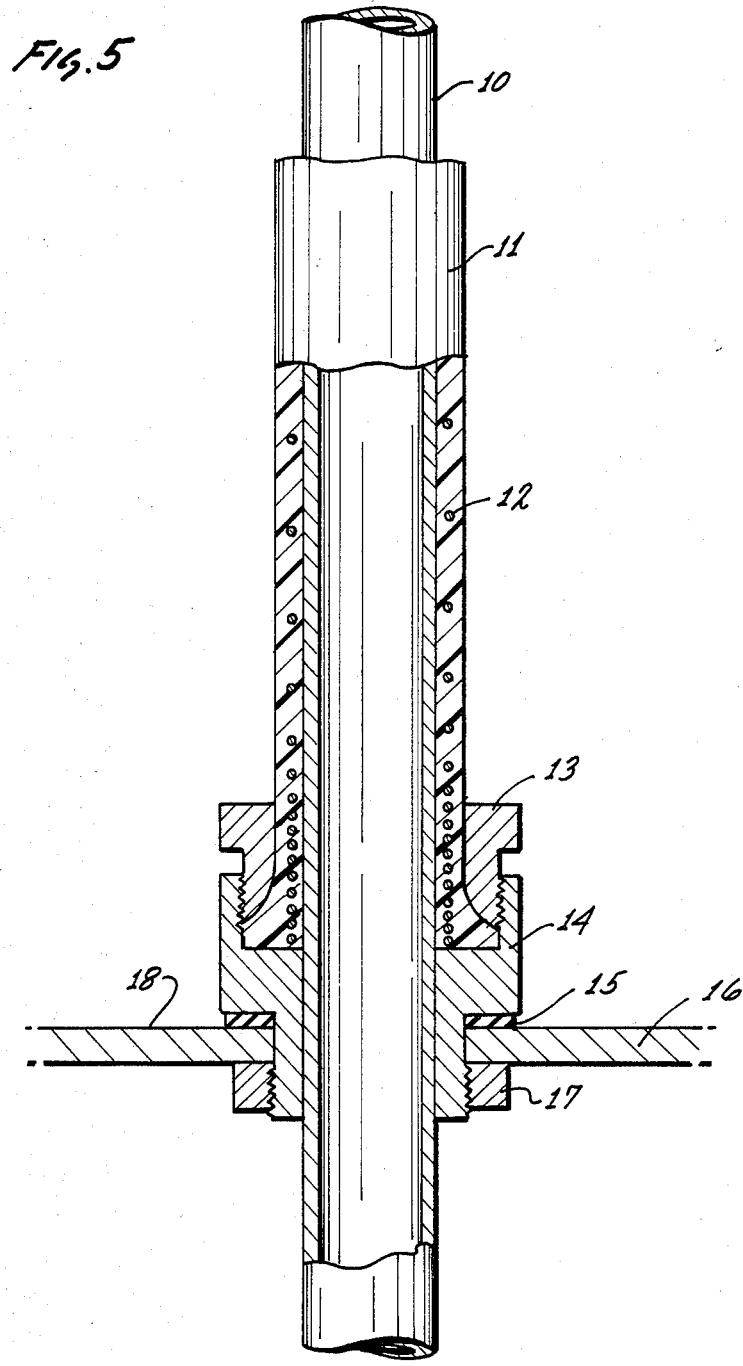

TAPERED TORQUE STRAIN RELIEF COUPLING

CROSS REFERENCE TO RELATED APPLICATIONS

We have not filed any other patent applications related to the invention disclosed in this application.

BACKGROUND

1. Field of the Invention

There are many applications requiring that a flexible member be securely attached to a rigid member. Examples of such applications include: flexible electrical wires attached to plugs or other connectors; flexible hydraulic or other hoses attached to rigid couplings; flexible ropes anchored at one end; flexible surgical tubing, or catheters, attached to rigid connectors; and fiber optic conductors attached to transducers or the like. In all such applications, the flexible member is subjected to varying degrees of flexing and stress, which flexing and stress the flexible member must withstand at the point of connection or attachment to the rigid member as well as elsewhere along its length. The point at which the flexible member is attached to the rigid member is at once a point of weakness and a point where stresses are likely to concentrate, and as a result this point is often the most likely point of failure or breakage of the flexible member or of its connection to the rigid member.

Strain relief devices, consisting in part of braided reinforcing strands arranged in various configurations, have in the past been used to attach a flexible member to a rigid member. Such devices have also been used to protect the flexible member from excessive flexing near the point of attachment. Many such devices act in the manner of a "Chinese Finger", in that the braided strands tighten on the flexible member when the flexible member is pulled. This is sometimes accomplished by weaving the braid in such a fashion that the spacing between adjacent strands is wide at the point of attachment of the braid to the rigid member, and progressively more narrow along the length of the flexible member as the distance from the point of attachment of the braid to the rigid member increases. However, unless the stress acts parallel to the flexible member, tending to pull it directly away from the rigid member, the "Chinese Finger" gives no relief. None of such devices have either addressed or solved the specific problem of reinforcing the flexible member at the point where it joins a rigid member so as to prevent breakage of the flexible member at that point, particularly with respect to stresses other than a straight pull away from the rigid member, and failure or breakage of flexible members at the point of attachment continues to be a major problem.

Whenever the terms "wide" or "open" weaving are used herein, said terms shall refer to a pattern of weaving in which the strands of the braid are relatively far apart from one another and in which the open spaces between strands are relatively large. The terms "narrow" or "close" weaving shall refer to a pattern of weaving in which the strands of the braid are relatively close to one another and in which the open spaces between the strands are relatively narrow.

2. Prior Art

Strain relief couplings which include, as one element, a woven braid or the like, have been disclosed in a variety of configurations.

Kellems Pat. No. 2,143,985 discloses a "cable grip", but the essence of that invention is a swivel-joint attachment for a flexible member so constructed that the flexible member can swivel even though it is rigidly held in place. A woven braid is used in this invention, but the braid functions only as a "Chinese Finger", tightening its grip if the flexible member is pulled. The problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

Kellems Pat. No. 2,189,987 pertains to "deformation control" and includes a woven braid. This invention uses either braid or other reinforcing members embedded within a resilient body, and the whole is constructed in such a manner that the resilient body will deform under stress in a desired direction or degree. The braid itself functions as a "Chinese Finger", tightening its grip if the flexible member is pulled. The problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

Canfield Pat. No. 2,939,905 discloses methods of connecting electrical conductors, in particular the use of flexible braided conductors to provide strength and good electrical contact at the point of attachment of the flexible conductor to the rigid member. The woven braid in this invention is a part of the flexible member rather than a separate element intended to grip it. The problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

Clay Pat. No. 3,291,507 pertains to a "support device", the essence of which is its ready detachability from the flexible member. As with the three patents listed above, the problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

Johnsen Pat. No. 3,487,160 pertains to the use of woven braid as an element of a cable splice. The problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

Damm Pat. No. 3,569,912 discloses an electrical conductor, enclosed within an armored sheath in which a woven braid is used to achieve greater rigidity, adapted for use on explosive ordnance. The problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

DiPalma Pat. No. 4,070,083 discloses the use of flexible braid as an element of an invention to relieve stress at the point of attachment of electrical wires to a plug. Although stress at the point of attachment is recognized as a problem, and it is an object of the invention to provide a means to solve the problem, the use of braid woven closely or narrowly at the point of attachment and more openly or widely as the distance from the point of attachment increases, so as to distribute stress, is not disclosed. In fact, in DiPalma's invention the braid does not even come into physical contact with the flexible cable either at the point of connection of the wires or at the point where the cable enters the plug housing; rather, the braid first contacts the cable at a point some distance down the length of the cable away from the plug housing, and the braid functions only to grip the cable, not to distribute stress.

Finally, Albert Pat. No. 4,367,967 discloses a method for restricting the radius of curvature of a flexible member at the point of attachment to a rigid member, but, as with the other patents cited above, the problem of alleviating and distributing the stress at the point of attachment of the flexible member to the rigid member is not an object of the invention, and the use of braid in which the weaving pattern is close or narrow at the point of attachment, and progressively more open or wide along the flexible member as the distance from the point of attachment increases, so as to distribute stress, is not disclosed.

SUMMARY OF THE INVENTION

In this invention, the end of a flexible member, at its point of attachment to a rigid member, is enclosed within a plurality of braided strands. The strands are very closely or narrowly woven at the point of attachment, and are more openly or widely woven as the distance from the point of attachment increases. At the point of attachment, the strands are spaced very close together and are nearly perpendicular to the flexible member, and at that point the braid is so stiff that its stiffness is just about equal to the stiffness of the rigid member itself. As the distance along the flexible member from the point of attachment increases, the weave of the braid becomes progressively more wide or open, and at the point of termination of the braid the stiffness of the braid has decreased so much that the stiffness of the combination of the braid and the flexible member is about the same as the stiffness of the flexible member by itself. In this fashion, stresses which would otherwise be concentrated at the point of attachment, and which would cause the breakage or failure of the flexible member, are by said structural design of the braid progressively distributed or tapered along the length of the flexible member so that the member can flex and "give" with the stress as distributed.

It is an object of this invention to provide means for reinforcing the end of a flexible member so that the stresses resulting from application either of torque (twisting force), or of bending (flexing) force, or both, are progressively distributed along the flexible member and not concentrated at the point where the flexible member is joined to a rigid immovable member.

Another object of this invention is to provide a strain relief which will be uniformly strong and resistant to pulling stress throughout its length.

Other objects and advantages of this invention will be apparent to those skilled in the art upon a consideration of the description and drawings herein.

DESCRIPTION OF THE DRAWINGS

FIG. 1 is a perspective view of an electrical cable protected by the Strain Relief at the point of attachment to an electric plug.

FIG. 2 is a front view of the assembly shown in FIG. 1.

FIG. 5 is a cross-sectional view of a flexible hose installed in a waterproof mount and reinforced at that point with the Strain Relief embedded within a resilient covering.

DESCRIPTION OF THE PREFERRED EMBODIMENT

Figure 3:
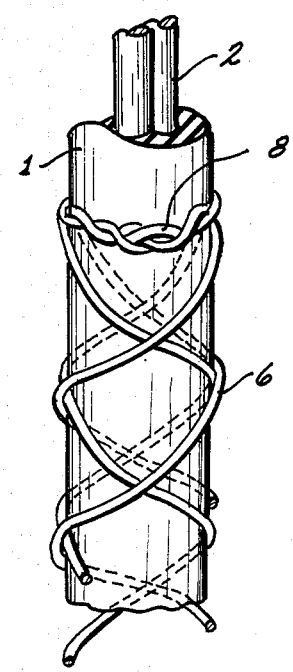
FIG. 3 shows an alternate embodiment in which the free end of the strands are woven together.

This invention protects a flexible member at the point where it is attached to a rigid member. The flexible member may be a rope, an electrical cable, a hose, a tube, a catheter, an artificial blood vessel, or the like.

In FIGS. 1 and 2, the flexible member 1 is an electrical cable with inner conductors 2. Cable 1 is attached to plug 3 by means of clamp 5 held by bolt 4. Flexible braid 6 reinforces the cable at the point of attachment to the plug, and collar 7 retains the ends of the strands of braid 6 in place.

Braid 6 is composed of a plurality of inelastic, flexible strands. The spacing between adjacent strands, at any given point, is a function of the distance between that point and the point of attachment of the flexible and rigid members. The apposition between the strands and the flexible member, or in other words the circumference of the braid itself, is constant. In FIG. 2, distance A represents the distance from the point of attachment C to the point at which the spacing between adjacent strands of the braid is to be determined, and spacing B represents the length of the space between adjacent strands at distance A from point of attachment C. In general, braid 6 is narrowly or closely woven at the point of attachment and progressively more openly or widely woven as the distance from the point of attachment increases. Thus, where distance A is small, space B will be very small, and as distance A increases, space B will also increase, although at a lesser rate.

In the preferred embodiment of the invention, the relationship between distance A and spacing B is a parabolic function given by the formula:

$$A = C_1 \times C_2 \times B^2$$

where:
- "A" is the distance from the point of attachment as shown in FIG. 2;
- "B" is the spacing between adjacent strands at point A, as shown in FIG. 2;
- "$C_1$" is a constant the value of which is determined by the diameter of the flexible member; and
- "$C_2$" is a constant the value of which is determined by the stiffness of the flexible member.

In another embodiment of the invention, spacing B is directly proportional to distance A and is given by the formula:

$$A = C_3 \times C_4 \times B$$

where:
- "A" is the distance from the point of attachment as shown in FIG. 2;
- "B" is the spacing between adjacent strands at point A, as shown in FIG. 2;
- "$C_3$" is a constant the value of which is determined by the diameter of the flexible member; and
- "$C_4$" is a constant the value of which is determined by the stiffness of the flexible member.

In an alternate embodiment of the invention, collar 7 as shown in FIG. 1 is omitted, and instead the free ends of the strands 8 are woven together, as shown in FIG. 3.

Figure 4:
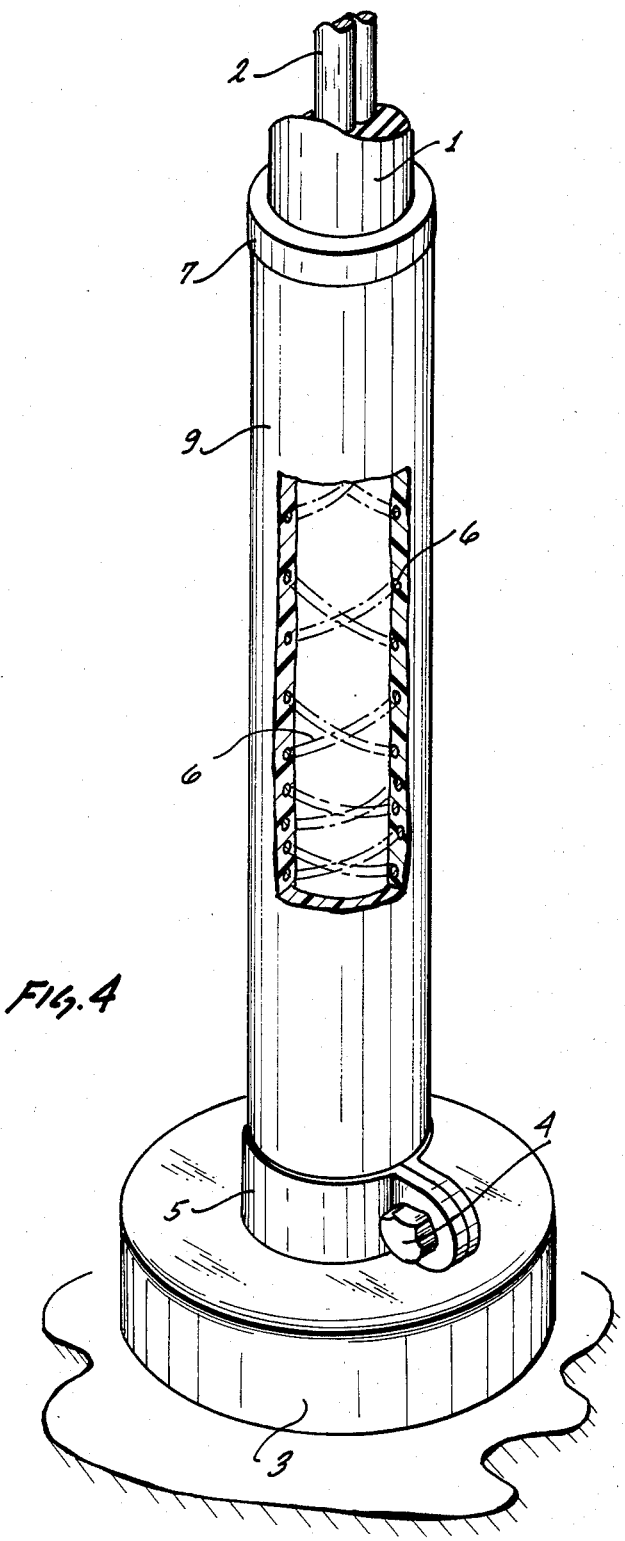
FIG. 4 is a perspective of an alternate embodiment in which the strands are embedded within a resilient covering.

In another embodiment of the invention as shown in FIG. 4, the strands 6 of the braid are embedded within a flexible sheath 9. Flexible sheath 9 is constructed with a diameter such that it fits tightly around flexible member 1, shown in the figure as an electrical cable with conductors 2, and the flexible sheath with the cable inside is clamped to plug 3 by clamp 5 secured by bolt 4. Collar 7 covers the free end of the sheath, or in some embodiments collar 7 may be omitted and the free ends of the braid woven together in the fashion illustrated in FIG. 3 but covered by sheath 9.

In yet another embodiment illustrated in FIG. 5, flexible member 10, shown as a hollow tube or catheter, passes through rigid member 16, shown as the wall or floor of a container of liquid. Strands 12 of the braid are embedded within sheath 11, and sheath 11 fits tightly around flexible member 10. Clamping means 14 and gasket 15 are secured to rigid member 16 by nut 17, and sheath 11 with flexible member 10 inside is held tightly in place within clamping means 14 by clamping nut 13. As in the other figures, the braid is closely or narrowly woven at the point of attachment between clamping means 14 and flexible member 10, and progressively more openly or widely woven as the distance from the point of attachment increases. In FIG. 5, strain relief is provided only on upper surface 18 of rigid member 16; however, it would be possible to provide similar relief on both sides of rigid member 16 by installing another Strain Relief on the lower side of rigid member 16.

Ordinarily, in an application in which a flexible member connected to a rigid member is repeatedly subjected to torque, twisting forces, bending forces, flexing forces, or the like, the effect of such forces is concentrated at the point of connection, and as a result failure most often occurs at that point. In this invention, the variation in the spacing between the braids, with the weaving close, or narrow, at the point of connection and progressively more open, or wider, as the distance from the point of connection increases, operates to distribute the stress over a substantial length of the flexible member. The stress, and its resulting strain, are thereby tapered from the point of connection with the rigid member over the length of the braid and the flexible member. Therefore, failure does not occur at the point of connection and the life of the assembly is greatly prolonged. The effect of forming the braid as disclosed in this invention is that, at the point of connection between the flexible and rigid members, there is no abrupt change in stiffness. Rather, at that point the braid is so closely or narrowly woven that it is nearly as stiff as the rigid member, and its stiffness gradually decreases as the distance from the point of connection increases, until, at the other end, the stiffness of the braid approximates or is even less than that of the flexible member itself.

This invention has many applications, of which the joining of electrical cables to plugs or other connectors, the connection of gasoline hoses to pumps or nozzles, the attachment of catheters or surgical tubing to medicinal apparatus and to tissue of the patient, and the connection of hydraulic hoses to fittings, are but a few examples.

Although this invention has been shown with respect to preferred embodiments, other embodiments, modifications, alterations and applications will be apparent to those skilled in the art.

Having thusly described the invention, We claim:

1. Reinforcing means adapted for reinforcing a flexible member extending from a rigid member, said reinforcing means comprising a plurality of strands braided in the shape of a hollow tube adapted to be disposed around the flexible member, said strands being closedly braided adjacent to the rigid member and progressively more openly braided around the flexible member as the distance along the flexible member from the point of attachment between the flexible member and the rigid member increases.

2. Reinforcing means according to claim 1 in which the open end of the braided strands is secured by a clamping means.

3. Reinforcing means according to claim 1 in which the spacing between adjacent strands at a given point is proportional to the square root of the distance between that point and the point of attachment of the flexible member to the rigid member.

4. Reinforcing means according to claim 1 in which the spacing between adjacent strands at a given point is directly proportional to the distance between that point and the point of attachment of the flexible member to the rigid member.

5. Reinforcing means according to claim 1 in which the strands are embedded within a flexible sheathing means.

6. Reinforcing means adapted for reinforcing an elongated flexible member extending from a rigid member, said reinforcing means comprising:
   a plurality of strands of flexible material braided to define an elongated hollow tube having a proximal extremity and a distal extremity and adapted to be disposed about the flexible member for location of said proximal extremity at a first point on said flexible member located adjacent said rigid member, and location of said distal extremity at a second point on said flexible member located remote from said rigid member, said strands being closely spaced adjacent said proximal extremity and progressively more greatly spaced apart as said strands proceed from said proximal extremity to said distal extremity whereby upon disposition of said reinforcing means upon said flexible member, said flexible member is resistant to flexure at said first point and progressively more subject to flexure toward said second point; and means for constraining said proximal extremity of said braided material against longitudinal movement relative to said flexible member.

7. Reinforcing means according to claim 6 in which said distal extremity of the braided strands is secured by a clamping means.

8. Reinforcing means according to claim 6 in which the spacing between adjacent strands at a given point is proportional to the square root of the distance between that point and said proximal extremity.

9. Reinforcing means according to claim 6 in which the spacing between adjacent strands at a given point is directly proportional to the distance between that point and said proximal extremity.

10. Reinforcing means according to claim 6 in which the strands are embedded within a flexible sheathing means.

11. In combination, a rigid member, an elongated flexible member connected to and extending from said rigid member, and reinforcing means adapted for reinforcing said flexible member, said reinforcing means comprising:

a plurality of strands of flexible material braided to define an elongated hollow tube having a proximal extremity and a distal extremity and adapted to be disposed about said flexible member for location of said proximal extremity at a first point on said flexible member located adjacent said rigid member, and location of said distal extremity at a second point on said flexible member located remote from said rigid member, said strands being closely spaced adjacent said proximal extremity and progressively more greatly spaced apart as said strands proceed from said proximal to said distal extremity whereby upon disposition of said reinforcing means upon said flexible member, said flexible member is resistant to flexure at said first point and progressively more subject to flexure toward said second point; and means for constraining said proximal extremity of said braided material against longitudinal movement relative to said flexible member.

12. Reinforcing means according to claim 11 in which said distal extremity of the braided strands is secured by a clamping means.

13. Reinforcing means according to claim 11 in which the spacing between adjacent strands at a given point is proportional to the square root of the distance between that point and said proximal extremity.

14. Reinforcing means according to claim 11 in which the spacing between adjacent strands at a given point is directly proportional to the distance between that point and said proximal extremity.

15. Reinforcing means according to claim 11 in which the strands are embedded within a flexible sheathing means.

* * * * *

UNITED STATES PATENT AND TRADEMARK OFFICE
CERTIFICATE OF CORRECTION

PATENT NO. : 4,509,877

DATED : April 9, 1985

INVENTOR(S) : Sidney S. Sobin

It is certified that error appears in the above-identified patent and that said Letters Patent is hereby corrected as shown below:

Claim 1, line 5, "closedly" should be --closely--.

Signed and Sealed this

Twenty-seventh Day of August 1985

[SEAL]

Attest:

DONALD J. QUIGG

*Attesting Officer*   *Acting Commissioner of Patents and Trademarks*